(12) United States Patent
Goldberg et al.

(10) Patent No.: US 6,464,970 B1
(45) Date of Patent: *Oct. 15, 2002

(54) METHOD AND COMPOSITION FOR PREVENTING SURGICAL ADHESIONS

(75) Inventors: Eugene P. Goldberg, Gainesville, FL (US); Yoseph Yaacobi, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/210,454

(22) Filed: Mar. 21, 1994

Related U.S. Application Data

(62) Division of application No. 08/026,125, filed on Mar. 3, 1993, now Pat. No. 5,350,573, which is a continuation of application No. 07/818,125, filed on Jan. 8, 1992, now abandoned, which is a division of application No. 07/696,960, filed on May 8, 1991, now Pat. No. 5,140,016, which is a continuation of application No. 07/555,377, filed on Jul. 19, 1990, now Pat. No. 5,080,893, which is a continuation of application No. 07/199,687, filed on May 31, 1988, now abandoned.

(51) Int. Cl.$^7$ .................. A61K 31/715; A61K 31/717; A61K 31/78; A61K 31/79
(52) U.S. Cl. .................. 424/78.08; 424/78.24; 424/78.31; 424/78.32; 424/78.38; 514/54; 514/57
(58) Field of Search .................. 424/78.24, 78.08, 424/78.32, 78.38, 78.31; 514/772.1, 54, 57, 772.5, 772.6, 781, 777

Primary Examiner—Edward J. Webman
(74) Attorney, Agent, or Firm—Miles & Stockbridge; Dennis P. Clarke

(57) ABSTRACT

An improved method and composition for preventing adhesions during surgery. Tissue surfaces and surgical articles involved in the surgery are coated with a solution of a hydrophilic, polymeric material prior to manipulation of the tissue during surgery. The composition comprises a solution of a polymeric material having a molecular weight of about 500,000 or above having a concentration of from about 0.01 to about 15%, by weight.

4 Claims, No Drawings

METHOD AND COMPOSITION FOR PREVENTING SURGICAL ADHESIONS

This is a division of application Ser. No. 08/026,125 filed Mar. 3, 1993, now U.S. Pat. No. 5,350,573, which is a continuation of application Ser. No. 07/818,125 filed Jan. 8, 1992 (abandoned), which is a division of application Ser. No. 07/696,960 filed May 8, 1991 (U.S. Pat. No. 5,140,016), which is a continuation of Ser. No. 07/555,377 filed Jul. 19, 1990 (U.S. Pat. No. 5,080,893), which is a continuation of Ser. No. 07/199,687 filed May 31, 1988 (abandoned).

BACKGROUND OF THE INVENTION

1. Field of the Invention

The present invention relates to the improvement of surgical techniques and tissue-protective surgical solutions.

2. Prior Art

Adhesions of the tissues involved in surgery occasioned by manipulative trauma of the tissue surfaces during the surgery and other causes such as drying and ischemic trauma constitute one of the most serious postoperative complications of surgical procedures.

Although a variety of techniques have been proposed to reduce adhesions, the problem continues to plague the art and seriously compromise even the finest and most scrupulously performed surgeries. Prior attempts to alleviate the problem and the disappointing results attendant are described in Davis et al, Surgery, Vol. 2, p. 877 (1937); Gozalez, Surgery, Vol. 26, p. 181 (1949); Hunter et al, J. Bone Joint Surg., Vol. 53A, p. 829 (1971); Ellis, Surg. Gynecol. Obst., Vol. 133, pp. 497–511 (1971); Lindsay et al, In Verdan, C. (ed); Tendon Surgery of the liand, Lond, Churchill Livingstone, pp. 35–39 (1979); Potenza, J. Bone Joint Surg., Vol. 45A, p. 1217 (1963); Verdan, J. Bone Joint Surg. Vol., 54A, p. 472 (1972); St. Onge et al, Clin.

Orthop., Vol. 148, pp. 259–275 (1900); Thomas et al, Clin. Orthop., Vol. 206, pp. 281–289 (May, 1986); Weiss et al, Bull. Hosp. Jt. Dis. Orthop. Inst., Vol. 46(1), pp. 9–15 (1986)].

Goldberg et al. [Arch. Surg., Vol. 115, pp. 776–780 (1980)] describes the use of certain hydrophilic polymer solutions (Povidone polyvinyl-pyrrolidone K-30 PVP, and dextran) to coat tissue exposed to drying and/or manipulative peritoneal trauma as well as the surgical articles, etc., which contact the tissue before and during surgery to prevent adhesions. Although the materials and methods of Goldberg et al showed some improvement over other research studies in which hydrophilic polymer solutions were used to attempt to reduce the incidence of surgical adhesions, there still exists significant need for improvement.

A distinct disadvantage associated with the materials and methods of Goldberg et al and other prior art which has shown some benefit is the required use of highly concentrated solutions of the polymeric materials which makes practical use in surgery very difficult. Concentrated polymer solutions (greater than about 10–15%), for example, the 25% PVP and dextran solutions used by Goldberg et al, become sticky due to drying during surgery on the surfaces of tissue, surgeons' gloves, instruments, etc. This can seriously interfere with normal surgical procedures. High concentrations of PVP (K-30-molecular weight about 40,000) and dextran (molecular weight about 300,000) were required to achieve even some degree of tissue protection. Many studies prior to the report of Goldberg et al used lower concentrations of PVP, dextran, or other water soluble polymers which were even more ineffective. For example, Ellis [Surg.

Gynecol. Obst., Vol. 133, pp. 497–5111 has stated that "use of PVP was accompanied by a slightly greater incidence of adhesions" in a rat peritoneal adhesions study. He also states that because "such macro-molecular solutions as plasma or dextran are known to be absorbed rapidly through functional lacunas on the under surface of the diaphragm" and "It is therefore probable that any effect of PVP or any other macro-molecular solution introduced into the peritoneal cavity could only be transitory". In the study by Berquist et al [Eur. Surg. Res., Vol. 9, p. 321 (1977)]using 10% dextran-70 (molecular weight 70,000) and 1% hyaluronic acid (molecular weight unknown) it was reported that there was "no difference between control and treated groups" for adhesions in rat and rabbit studies. Even attempts to use the relatively low molecular weight dextran-70 at very high concentrations (32%), based on suggestions of some beneficial effect in reducing genital tract adhesions in female rabbits (Neuwirth et al, Am. J. Obstet. Gynecol., Vol. 121, p. 420 (1974)] have not proven very successful. A commercial 32% (w/v) solution of dextran-70 was introduced as a hysteroscopy fluid about 1984, but recent studies have shown "no effect in reducing adhesions" using 32% dextran [Hadick et al, Military Medicine, Vol. 152, p. 144 (1987)].

Moreover, the use of such high concentrations may increase the expense of the surgical solutions and poses problems in preparing, purifying, stabilizing and storing solutions of such highly concentrated and often viscous solutions. For example, 32% dextran tends to crystallize "when subjected to temperature variations or when stored for long periods" [data sheet for commercial 32% dextran-70 solution].

Although the studies reported by Goldberg et al indicated some modest improvement in preventing adhesions using 25% PVP (mol. wt. 40,000) and a slight improvement with 25% dextran (mol. wt. 300,000) even using a surgical method involving coating of tissues and surgical implements before surgical manipulation, the materials and surgical solutions used were clearly impractical for clinical use in surgery.

It is, therefore, an object of the present invention to provide a significant improvement in compositions and method of use in surgery for preventing surgical adhesions.

SUMMARY OF THE INVENTION

The above and other objects are realized by the present invention which provides an improved method of preventing surgical adhesions in tissue by manipulation thereof during surgery comprising coating tissue surfaces involved in the surgery and/or the surfaces of surgical articles which contact the tissue surfaces during the surgery with an aqueous solution of a hydrophilic, polymeric material selected from the group consisting of water soluble, biocompatible, pharmaceutically acceptable polypeptides, polysaccharides, synthetic polymers, salts and complexes thereof and mixtures thereof prior to manipulation of the tissue during the surgery, the improvement wherein the hydrophilic, polymeric material is of high molecular weight (greater than 500,000) and the solution contains from about 0.01% to about 15%, by weight, of the polymeric material.

The invention further comprises certain compositions, specifically adapted for coating the surfaces of tissues involved in surgery and preferably also the surfaces of articles which contact the tissue surfaces during the surgery to prevent surgical adhesions in the tissue by manipulation or drying thereof during surgery, consisting essentially of a pharmaceutically acceptable aqueous solution of a hydrophilic, polymeric material of high molecular weight (>500,000) selected from the group consisting of pharmaceutically acceptable polypeptides, polysaccharides, synthetic polymers and salts and complexes thereof and mixtures thereof. Where the polymeric material is a polysaccharide solutions according to the invention containing from about 0.01 to less than about 1%, by weight, of the polysaccharide have been found to be highly advantageous. Where the polymeric material is a polypeptide or other synthetic polymer, solutions according to the invention containing from about 0.01 to less than about 1.5%, by weight, thereof may be employed.

An additional embodiment of the invention comprises a surgical article, surfaces of which are adapted for contacting tissue surfaces during surgery having a coating thereon formed from a composition described above.

DETAILED DESCRIPTION OF THE INVENTION

The present invention is predicated on the discovery that surgical adhesions may be prevented to a far greater extent than previously achieved by ensuring pre-coating of the involved tissues prior to the surgical manipulation thereof with the above described solutions. Pre-coating of all surgical articles destined for contact with the involved tissue wherein the coating solution has the composition defined above is a further beneficial preferred embodiment of the invention.

The novel compositions of the invention unobviously reduce the incidence of surgical adhesions to a far greater degree than would be expected from a reading of the extensive literature in this field.

It has been found, as demonstrated hereinbelow, that combined use of the high molecular weight hydrophilic polymer solutions in the low concentration range described herein results in an unexpected significant decrease in the risk of surgical adhesions.

The unexpected benefit of using the polymer compositions of this invention with pre-coating of the involved tissue has been clearly shown to give far better results than post-operative or post-tissue manipulative treatment or coating.

Furthermore, the surprisingly advantageous tissue-protective adhesions preventive properties of the compositions of this invention have been demonstrated when used to coat tissue prior to surgical manipulation even when conventional irrigating solutions are subsequently used during surgery.

For purposes of the present invention, the following definitions are applicable. "Surfaces" refers to the surfaces of all tissue involved in and subject to manipulation by a foreign object during surgery or exposed to traumatic drying in the surgical field as well as the surfaces of all surgical articles used in surgery and which may contact the involved tissue. "Involved tissue" refers to all tissue involved in and subject to manipulation by a foreign object during surgery or exposed to traumatic drying in the surgical field.

"Surgical articles" refer to all instruments, devices, accessories, swabs, sponges, gauzes, gloves, sutures, etc., used in surgery and which may contact the "involved tissue". "Surgery" refers to all invasive, surgical techniques which expose "tissue" subject to surgical adhesions.

"Manipulation" refers to all contact with "involved tissue" which causes surgical adhesions. "Surgical adhesions" refers to the collagenous connective tissue which develops post-operatively after manipulative trauma to the "involved tissue". Also defined by this term are adhesions produced from "involved tissue" due to drying and/or ischemic trauma during the surgical procedure.

"Hydrophilic, polymeric material" refers to all pharmaceutically acceptable macromolecular materials, synthetic or natural, which are hydrophilic and non-toxic and non-immunogenic to "involved tissue".

"Coating formed from the aqueous composition" refers to the "wet" coatings formed on the coated surfaces using the aqueous composition as well as coatings formed from the aqueous composition which are dried and may be subsequently re-wetted to produce the wet coating.

In general, there is extensive literature on attempts to use various hydrophilic polymer solutions to prevent surgical adhesions by applying such solutions to the tissue surfaces in the surgical field following manipulative procedures and tissue trauma and just prior to wound closure. The concept guiding such studies has been that the viscous polymer solutions might afford a protective barrier to bridging of the traumatized tissues by collagenous connective tissue (adhesions). Polyvinylpyrrolidone (PVP), carboxymethylcellulose (CMC), dextran (dex), and hyaluronic acid (IIA) have all been investigated, but no 35 clinically practical results have been achieved.

The present invention is predicated on the discovery that a major improvement in adhesion prevention is surprisingly achieved with aqueous hydrophilic polymer solutions of very high molecular weight (>500,000), using a method of tissue protection involving the application of the polymer solution to the tissue before surgical manipulative procedures are initiated. This combination of materials and method of use results in uniquely successful tissue protection and prevention of surgical adhesions and overcomes the drawbacks of the prior art where either (1) the polymers used (i.e., PVP or dextran) have been of molecular weights less than 500,000 necessitating high concentrations (>20%) to have any beneficial effect and therefore exhibiting impractical sticky properties during surgery and/or (2) the solutions have been used by a method involving coating of tissues at the conclusion of surgery thus not affording the tissue protection during surgery which is provided by the method of this invention. Thus, by the combined use of (a) more dilute aqueous hydrophilic polymer solutions made possible with polymers having molecular weights greater than 500,000 and (b) a method of use wherein the solution is used as a tissue protective coating at the beginning of surgery, it has been discovered that a major improvement in preventing surgical adhesions, which is clinically practical, is achieved.

Although, in theory, virtually any biocompatible, water soluble, polymer (e.g., polysaccharides, polypeptides, carbohydrates, synthetic polymers and their salts) of very high molecular weight (>500,000) may be used to produce the tissue-protective aqueous solutions of this invention, polyvinylpyrrolidone (PVP), carboxymethylcellulose (CMC), and hyaluronic acid and its salts (HA) are particularly effective. However, because HA and related polysaccharides are natural constituents of cell membranes and tissues, exhibit exceptional biocompatibility and are effective at extremely low concentrations, HA solutions represent a preferred embodiment of this invention.

This invention is predicated on the use of the dilute high molecular weight polymer solutions described herein.

Polyvinylpyrrolidones reported in attempts to reduce adhesions heretofore (i.e., K-30 or K-40) have been of molecular weights substantially less than 500,000 and have been ineffective at lower concentrations (<20%) or sticky and impractical at higher concentrations where some benefit has been reported.

The PVP materials of this invention have substantially greater weight average (Mw) or viscosity average (Mv) molecular weights than 500,000. These include K-90 PVP (having a reported Mw or Mv molecular weight of about 1,000,000) or high molecular weight PVP made by gamma radiation polymerization, of N-vinylpyrrolidone (gamma-PVP). Although high Mv PVP such as K-90 may be used in the method of this invention at concentrations of 10–15%, it is preferred to use gamma-PVP which may be prepared with Mv substantially greater than 1,000,000 (to Mv of 5,000,000 or more). Gamma-PVP of extremely high Mv is advantageous in that it may be used at concentrations of 5% or less. Various bioacceptable PVP and gamma-PVP copolymers may also be used in the practice of the invention. Furthermore, other highly purified bioacceptable, high molecular weight synthetic hydrophilic polymers, e.g., polyethylene glycol, dimethylacrylamide, and the like, may be used in this invention. It is also within the scope of this invention to utilize gamma-PVP which is prepared in combination with the other above-mentioned synthetic polymers, proteins or polysaccharides of this invention.

The carboxymethylcelluloses (CMC) useful in combination with the novel method of use in this invention are also of molecular weights greater than 500,000. A preferred example is a commercially available CMC of about 800,000 molecular weight. Such polyelectrolyte polysaccharides are especially valuable because of the good viscoelastic behavior of aqueous solutions which enable the use of lower solution concentrations for effective tissue protection; aqueous solutions with concentrations of 1–2% or less by the method of this invention.

Naturally occurring polysaccharides which occur in cartilage, soft tissues, and cell membranes such as hyaluronic acids and its salts (HA) are especially effective as tissue-protective adhesion preventing agents using the method of this invention. Although naturally occurring HA with molecular weight greater than 1,000,000 has been used clinically as a gel in ophthalmic surgery to maintain the anterior chamber, such gels require HA concentrations of 1.0% or more and because of their extremely high viscosity are not readily applied as tissue-protective irrigating solutions according to the method of this invention. Additionally, because of the high cost of ophthalmic HA gels, it has been impractical to consider any surgical application involving more than 1–2 ml of a 1% solution. Unexpectedly, we have discovered that dilute Ha solutions of HA with molecular weight >500,000 are highly effective at concentrations of 0.01 to 0.6%, by weight, when used for surgical adhesion prevention by our method of application. Such dilute HA solutions therefore represent uniquely efficient materials for the method of this invention because of the excellent biocompatibility, favorable non-Newtonian rheology and tissue coating by very dilute solutions, practical cost for general surgical applications which may require 200–300 ml of the dilute solutions, and exceptional adhesion prevention qualities when combined with the method of use according to the invention. As indicated in the following examples, even a 0.01% solution of about 1,500,000 molecular weight HA effectively prevents all severe intra-abdominal adhesions in a rat adhesions model that normally produces more than 70% adhesions.

Virtually all types of surgery in which post-operative adhesions represent a significant complication (e.g., peritoneal, pericardial, obstetric, gynecological, neurological, arthroscopic, orthopedic, plastic, reconstructive, muscle or tendon) are susceptible to modification and improvement according to the present invention. Important examples include abdominal, thoracic, cardiovascular, ob/gyn, and neurosurgical procedures, all of which are fraught with potentially severe post-operative complications which may be attributed to surgical trauma. In the case of cardiac surgery involving transplants, vascular repair and by-passes, valve replacements, etc., reoperations continue to increase every year with repeat coronary artery surgery comprising the majority of such reoperations. Post-operative pericardial adhesions from initial surgery are common and subject patients undergoing repeat cardiac surgery to substantial risks. Potential injury to the heart, great vessels and extracardiac grafts during resternotomy as well as prolonged operative time increase morbidity and mortality. Resternotomy is associated with as much as a 6% incidence of major vascular injury and a more than 35% mortality has been reported for patients experiencing major hemorrhage during resternotomy. A 50% mortality has been reported for associated injuries to aortocoronary grafts. Pediatric cardiac surgery is also associated with a very high incidence of reoperations. In view of the marked increase in cardiac surgery and reoperations and the potentially serious complications related to pericardial adhesions, prevention of such adhesions represents a major health care need. The significant reduction in pericardial adhesions made possible by the materials and method of this invention is illustrated in the following examples.

Peritoneal adhesions represent another major health care problem with potentially serious post-operative complications associated with all types of abdominal surgery; with a reported incidence of 50–90% for laparotomies. As indicated in the following examples, a dramatic reduction in abdominal adhesions is made possible and clinically practical by the use of the materials and method of this invention.

EXAMPLE 1

This example illustrates the high incidence of peritoneal adhesions observed using a rat abdominal surgery model involving normal laparotomy with controlled cecal abrasion to afford an example of severe tissue trauma in such surgery and to be a control for comparison with the adhesions preventive materials and method of use of this invention.

Sprague Dawley rats weighing 250–300 gr were used in these peritoneal adhesion experiments. Fifteen animals were treated with a widely used sterile, commercially available, surgical irrigating solution, Ringer's lactate (RL).

Each animal underwent laparotomy through a midline incision after being anesthetized (I.M. injection of Ketamine, 100 mg/kg, and Xylazine, 11 mg/kg), prepped and draped in a sterile fashion. The cecum was exposed and irrigated with RL solution. The distal portion of this organ then was abraded, in a consistent manner using gauze sponges soaked with RL solution. Intraabdominal irrigation with the RL solution was done before incision of peritoneum, prior to contact with and during exposure and manipulation of internal organs, and before closure of the abdomen using a total of 10–12 ml of RL. Closure was performed in two layers, with 3–0 Vicryl® sutures. Two weeks later the animals were subjected to reoperations in which the peritoneal cavity was examined for the presence of adhesions. Adhesions were graded according to the following 0–4 scale.

0—No adhesions

1—Filmy, mild, adhesions, easily removed by blunt dissection (mild)

2—Fibrous adhesions, easily dissected (moderate)

3—Thick adhesions, dissectable (severe)

4—Thick adhesions, not dissectable without damage to adherent tissue (very severe).

Animals with adhesions which were scored at 2 or greater were regarded as exhibiting significant adhesions. For this adhesion control group which is representative of abdominal surgery with a well-defined cecal trauma, 11 of 15 animals (73%) exhibited significant adhesion formation, each with scores of 2 or more.

EXAMPLE 2

This example illustrates the significant advantages achieved by combined use of the high molecular weight hydrophilic polymer solutions of this invention and the surgical method of use which involves irrigation with the solutions at the beginning of surgery prior to any significant manipulation of tissue. The abdominal surgery rat model of Example 1 was used with the following aqueous CMC and PVP polymer solutions (concentrations are weight %):

1.0% CMC (Hercules 7H3SF, Mol. wt. ca. 800,000)

1.5% CMC

10% PVP/K-90 (BASF Kollidon, Mv ca. 1,100,000)

15% PVP/K-90

5.0% Gamma-PVP (prepared using 10% NVP with 0.05 Mrad gamma radiation, Mv >3,000,000).

The surgical protocol of Example 1 was used with CMC or PVP solutions administered instead of the Ringer's lactate. A significant reduction in the incidence of abdominal adhesions was noted as summarized below:

| Test Solution | # of Test Animals | Significant % Adhesions (Scored 2 or greater) |
| --- | --- | --- |
| 1.0% CMC | 14 | 21% |
| 1.5% CMC | 20 | 5% |
| 10% PVP/K-90 | 5 | 0% |
| 15% PVF/K-90 | 5 | 20% |
| 5.0% Gamma-PVP | 10 | 0% |

It is clear that using the method of this invention (tissue coating prior to surgical manipulation) the above solutions all effect a major reduction in adhesions as compared with the 73% adhesions exhibited by the control group of Example 1 using a conventional surgical irrigation solution in the same procedure.

EXAMPLE 3

This example illustrates the significant reduction in adhesions achieved by the use of the aqueous high molecular weight hyaluronic acid (HA) solutions with the surgical method of this invention. The abdominal surgery rat procedure of Example 1 was used with aqueous test solutions prepared at various concentrations (wt. %) with sodium hyaluronate (Genzyme, mol. wt. ca. 1,500,000). The following summarizes the scoring of adhesions for the HA solutions:

| Test Solution | # of Test Animals | Significant % Adhesions (scored 2 or greater) |
| --- | --- | --- |
| 0.05% HA | 10 | 10% |
| 0.1% HA | 10 | 0% |
| 0.3% HA | 18 | 17% |
| 0.6% HA | 19 | 0% |
| 0.8% HA | 10 | 10% |
| Ringer's lactate (control) | 15 | 73% |

Using the method of this invention (tissue coating prior to surgical manipulation), the HA solutions effect a major reduction in surgical adhesions, even at extremely low concentrations (no significant adhesions with 0.1% HA) as compared with 73% of significant adhesions for the control group of Example 1 in which a conventional surgical irrigating solution was employed in the same procedure.

EXAMPLE 4

This example illustrates the importance of using the polymer solutions of this invention in combination with the method of this invention for effective prevention of surgical adhesions. This is demonstrated by using 1.5% CMC and 0.6% HA solutions according to the method suggested by the prior art, i.e., irrigation with the solution at the conclusion of surgery prior to closure.

As in Example 1, each rat underwent laparotomy through a midline incision after being anesthetized (I.M. injection of Ketamine, 100 mg/kg, and xylazine, 11 mg/kg), prepped and draped in a sterile fashion. The cecum was located, exposed and its distal portion abraded in a standard consistent manner using dry gauze sponge. However, in this example, Intraabdominal irrigation with the test solution (10–12 ml per animal) was applied before closure of the abdomen; performed in two layers, with 3–0 Vicryl sutures as before. Two weeks later the animals were subjected to reoperations in which the peritoneal cavity was examined for the presence of adhesions which were graded according to the 0–4 scale. The results are summarized as follows:

| Test Solution | # of Test Animals | % Significant Adhesions (scored 2 or greater) |
| --- | --- | --- |
| Ringer's lactate (control) | 10 | 80% |
| 1.5% CMC | 10 | 70% |
| 0.6% HA | 10 | 80% |

These results demonstrate very clearly that using this severe animal model for surgical adhesions, there is no observed benefit to the use of the aqueous polymer solutions of this invention if used according to conventional or prior art methods. Using the method of this invention, however, the polymer solutions effect a dramatic reduction in adhesions as shown in Examples 2 and 3.

EXAMPLE 5

This example illustrates the surprisingly beneficial qualities of the hydrophilic polymer solutions of this invention when used by the method of this invention (i.e., coating of tissues prior to surgical manipulation) even when this is followed by the use of conventional surgical irrigating solutions such as physiological or normal saline or Ringer's lactate and without further use of the polymer solutions prior to closure.

As in Example 1, each rat underwent laparotomy through a midline incision after being anesthetized (I.M. injection of Ketamine, 100 mg/kg, and xylazine, 11 mg/kg), prepped and draped in a sterile fashion. The cecum was located, exposed and irrigated with the test solution. The distal portion of this organ then was abraded, in a standard consistent manner using solution-soaked gauze sponges. Intraabdominal irrigation with the test solution (ca. 6 ml per animal) was done before incision of peritoneum, prior to contact, exposure and manipulation of internal organs. Ringer's lactate solution (6 ml per animal) was applied before closure of the abdominal wall, performed as in other examples in two layers, with 3–0 Vicryl sutures. Two weeks later the animals were subjected to reoperations in which the peritoneal cavity was examined for presence of adhesions which were graded according to the 0–4 scale.

The following results show very surprising effectiveness of the high molecular weight polymer solutions of this invention in inhibiting post-operative adhesions when applied to tissues prior to the surgical procedure and surgical manipulation of tissue even when a conventional surgical irrigating solution is used before closure:

| Test Solution | # of Test Animals | % Significant Adhesions (scored (2 or greater) |
|---|---|---|
| Ringer's lactate (control) | 15 | 73% |
| 1.5% CMC | 9 | 11% |
| 0.6% HA | 10 | 10% |

EXAMPLE 6

This example illustrates the effectiveness of the aqueous polymer solutions and method of this invention in reducing pericardial adhesions in open heart and thoracic surgery using 1.0% CMC in a pericardial dog adhesion model. The following surgical procedure was followed:

Ten mongrel dogs weighing 15–20 kgs were divided into two groups of 5 each. One group was treated with a 1.0 wt. % aqueous solution of CMC (Hercules 7H3SF, mol. wt. ca. 800,000) and the other was treated with Ringer's lactate (RL) solution to serve as a control group.

Dogs were anesthetized initially with Biotal (0.04 mg.kg, I.V.). General anesthesia was maintained with 2% Enthrane and controlled ventilation following tracheal intubation. Each dog underwent a left thoracotomy through an incision at the fifth intercostal space, followed by ipsilateral pericardiotomy. Upon exposure of epicardium and prior to manipulation of internal organs, the pericardial sac was thoroughly irrigated with 20 ml of the test solution. The epicardium and the inner surface of the pericardium on the left side were abraded with 20 strokes of a gauze sponge wet with test solution to induce a hemorrhagic lesion. The pericardial sac was irrigated three times, each time with 20 ml of solution (60 ml total): immediately following pericardiotomy, 15 minutes follow-pericardiotomy, and prior to pericardial closure. After the epicardium and inner surface of the pericardium had been exposed for 30 minutes, to simulate intra-operative dessication, the pericardium was closed loosely with 2–0 silk sutures. Thoracotomy closure was performed in the usual fashion including aspiration of air and fluid from the left chest. Intercostal nerve blocks were induced with 1% Xylocaine and 1/100,000 epinephrine. All dogs received normal diets postoperatively.

Six weeks later the animals were subjected to reoperation. Bilaterial thoracotomies, under general anesthesia, with subsequent pericardiotomy were performed and the pericardial cavity was examined. Two independent observers unaware of the study solutions used in each animal evaluated the extent and severity of pericardial adhesions on the 0–4 grading scale. All animals were sacrificed and biopsies of abraded and unabraded epicardium along with those of the pericardium underwent histological evaluation.

The CMC treated group showed a marked reduction in pericardial adhesions as compared with the RL control group; 20% adhesions scored 2 or greater for the CMC group compared with 100% scored 2 or greater for the RL group. Histological sections of epicardium and pericardium which were evaluated for thickness, inflammation, fibrosis and neovascularity revealed no statistical differences in any parameter comparing the CMC solution with the RL control solution. These results confirm the effectiveness and safety of using the polymeric materials and method of this invention for prevention of pericardial adhesions.

The hydrophilic, polymer material may be dissolved in any suitable aqueous solution conventionally employed in surgery, e.g., Ringer's lactate, normal saline, or any other isoosmolar physiological medium.

What is claimed is:

1. In a method of preventing surgical adhesions of tissue in surgery comprising coating surfaces involved in said surgery with an aqueous solution of a hydrophilic, polymeric material prior to manipulation of said tissue during said surgery wherein said polymeric material is a member selected from the group consisting of water-soluble, biocompatible, pharmaceutically acceptable polysaccharides, excluding hyaluronic acid having a molecular weight above about 1.500.000, synthetic polymers, salts and complexes thereof and mixtures thereof, the improvement wherein said hydrophilic, polymeric material (1) has a molecular weight of about 500,000 or above, and (2) has a concentration in said aqueous solution in the range of from about 0.01% to about 15%, by weight.

2. In a method of preventing surgical adhesions of tissue in surgery comprising coating the surfaces of tissue involved in said surgery with an aqueous solution of a hydrophilic, polymeric material prior to manipulation of said tissue during said surgery wherein said polymeric material is a member selected from the group consisting of water-soluble, biocompatible, pharmaceutically acceptable polypeptides, polysaccharides, excluding hyaluronic acid having a molecular weight above about 1.500,000. synthetic polymers, salts and complexes thereof and mixtures thereof, the improvement wherein said hydrophilic, polymeric material (1) has a molecular weight of about 500,000 or above, and (2) has a concentration in said aqueous solution in the range of from about 0.01% to about 15%, by weight.

3. In a method of preventing surgical adhesions of tissue in surgery comprising coating the surfaces of surgical articles which contact tissue surfaces involved in said surgery with an aqueous solution of a hydrophilic, polymeric material prior to manipulation of said tissue during said surgery wherein said polymeric material is a member selected from the group consisting of water-soluble, biocompatible, pharmaceutically acceptable polysaccharides, excluding hyaluronic acid having a molecular weight above about 1,500.000. synthetic polymers, salts and complexes thereof and mixtures thereof, the improvement wherein said hydrophilic, polymeric material (1) has a molecular weight of about 500,000 or above, and (2) has a concentration in said aqueous solution in the range of from about 0.01% to about 15%, by weight.

4. The method of claim 1 wherein said surgery is peritoneal, pericardial, obstetric, gynecological, neurosurgical, arthroscopic, orthopedic, plastic, reconstructive, muscle or tendon.

* * * * *

UNITED STATES PATENT AND TRADEMARK OFFICE
CERTIFICATE OF CORRECTION

PATENT NO.     : 6,464,970 B1
DATED          : October 15, 2002
INVENTOR(S)    : Eugene P. Goldberg et al.

It is certified that error appears in the above-identified patent and that said Letters Patent is hereby corrected as shown below:

<u>Column 10,</u>
Lines 38, 52 and 67, "1.500.000" should read -- 1,500,000 --.

Signed and Sealed this

Eighteenth Day of February, 2003

JAMES E. ROGAN
*Director of the United States Patent and Trademark Office*